US009226986B2

(12) United States Patent
Gray-Dreizler et al.

(10) Patent No.: US 9,226,986 B2
(45) Date of Patent: Jan. 5, 2016

(54) SURGICAL STERILIZING CONTAINER AND SURGICAL FLUID EXTRACTION DEVICE

(71) Applicant: Aesculap AG, Tuttlingen (DE)

(72) Inventors: John Gray-Dreizler, Rottweil (DE); Dieter Weisshaupt, Immendingen (DE); Stefan Schuster, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 14/333,853

(22) Filed: Jul. 17, 2014

(65) Prior Publication Data

US 2014/0348722 A1 Nov. 27, 2014

Related U.S. Application Data

(63) Continuation of application No. PCT/EP2013/053530, filed on Feb. 22, 2013.

(30) Foreign Application Priority Data

Mar. 5, 2012 (DE) .......................... 10 2012 101 832

(51) Int. Cl.
*A61L 2/16* (2006.01)
*A61B 19/02* (2006.01)
*A61L 2/26* (2006.01)

(52) U.S. Cl.
CPC ................. *A61L 2/16* (2013.01); *A61B 19/026* (2013.01); *A61L 2/26* (2013.01); *A61B 2019/0213* (2013.01); *A61B 2019/0229* (2013.01); *A61L 2202/182* (2013.01)

(58) Field of Classification Search
CPC ........... A61B 19/026; A61L 2/07; A61L 2/16
USPC .......................................................... 422/292
See application file for complete search history.

(56) References Cited

U.S. PATENT DOCUMENTS 2,673,379 A 3/1954 Jewell et al.
3,437,423 A 4/1969 Mondiadis
(Continued)

FOREIGN PATENT DOCUMENTS

DE 37 11 621 10/1987
DE 3929906 C1 * 12/1990
(Continued)

OTHER PUBLICATIONS

English Translation of Document No. EP 0336047 A1 provided by espacenet.com: Mercey; Oct. 11, 1989.*
(Continued)

*Primary Examiner* — Kevin Joyner
*Assistant Examiner* — Holly Mull
(74) *Attorney, Agent, or Firm* — Lipsitz & McAllister, LLC

(57) ABSTRACT

A surgical sterilizing container is provided, having a bottom and a container wall. A through-opening is formed on the sterilizing container for the exchange of media. A valve device having an outlet valve is provided for opening and closing the through-opening. In order to remove fluid which has formed in the container interior while reducing the risk of germs penetrating into the container interior, the through-opening is formed in the container wall at a distance from the bottom, and the sterilizing container has a fluid lifting device for providing a fluid connection from the bottom to the outlet valve and for lifting fluid from the bottom to the outlet valve. A surgical fluid extraction device is also provided for use with a surgical sterilizing container having a container wall and a bottom.

20 Claims, 7 Drawing Sheets

(56) References Cited

U.S. PATENT DOCUMENTS

| | | | |
|---|---|---|---|
| 4,247,517 A | 1/1981 | Sanderson et al. | |
| 4,251,482 A | 2/1981 | Sanderson et al. | |
| 4,416,417 A | 11/1983 | Sanderson et al. | |
| 4,671,943 A | 6/1987 | Wahlquist | |
| 4,900,519 A | 2/1990 | Nichols | |
| 5,366,693 A * | 11/1994 | Burgos et al. | 422/26 |
| 5,441,707 A | 8/1995 | Lewis et al. | |
| 5,869,000 A | 2/1999 | DeCato | |
| 5,971,152 A | 10/1999 | Bowsman | |
| 6,150,159 A * | 11/2000 | Fry | 435/304.1 |
| 6,367,651 B2 | 4/2002 | Laib et al. | |
| 6,620,390 B1 | 9/2003 | Wagner | |
| 6,821,286 B1 | 11/2004 | Carranza et al. | |
| 7,641,852 B1 | 1/2010 | McPhail et al. | |
| 2001/0047997 A1 | 12/2001 | Laib et al. | |
| 2011/0262301 A1 | 10/2011 | Ghelman et al. | |
| 2013/0175276 A1 | 7/2013 | Gleichauf et al. | |

FOREIGN PATENT DOCUMENTS

| | | |
|---|---|---|
| DE | 198 27 442 | 12/1998 |
| DE | 197 53 671 | 6/1999 |
| DE | 198 30 460 | 11/1999 |
| DE | 600 11 879 | 8/2005 |
| DE | 10 2004 028 040 | 10/2005 |
| EP | 0336047 A1 * | 10/1989 |
| EP | 1 016 369 | 7/2000 |
| EP | 1 035 873 | 6/2002 |
| EP | 1 647 285 | 4/2006 |
| FR | 2 542 200 | 9/1984 |
| WO | WO 99/27969 | 6/1999 |
| WO | WO 2008/061137 | 5/2008 |
| WO | WO 2012/038314 | 3/2012 |

OTHER PUBLICATIONS

English Translation of Document No. DE 3929906 C1 provided by espacenet.com; Schnepple; Dec. 13, 1990.*

* cited by examiner

US 9,226,986 B2

SURGICAL STERILIZING CONTAINER AND SURGICAL FLUID EXTRACTION DEVICE

CROSS-REFERENCE TO RELATED APPLICATIONS

This application is a continuation of international application number PCT/EP2013/053530, filed on Feb. 22, 2013, and claims the benefit of German application number 10 2012 101 832.4, filed Mar. 5, 2012, which are incorporated herein by reference in their entirety and for all purposes.

FIELD OF THE INVENTION

The present invention relates to a surgical sterilizing container, comprising a bottom and a container wall, a through-opening for the exchange of media being formed on the sterilizing container, and comprising a valve device having an outlet valve for opening and closing the through-opening.

The invention also relates to a surgical fluid extraction device for use with a surgical sterilizing container having a container wall and a bottom.

BACKGROUND OF THE INVENTION

Surgical sterilizing containers of the kind mentioned at the outset are known, in which surgical instruments can be held for sterilization. During the sterilization process, fluid, in particular, condensate forms in a container interior defined by the sterilizing container. The condensate can be evaporated, for example, during a drying phase following the sterilization process. The steam can exit from the container interior via a through-opening which is formed on the sterilizing container and is openable and closable by the outlet valve.

As condensate usually collects on the bottom of the sterilizing container, sterilizing containers have been developed in which the through-opening is formed in the bottom and the outlet valve can open and close the through-opening in the bottom. This serves to drain the condensate which has collected on the bottom from the sterilizing container to the outside. The draining of condensate, in particular, when a pressure-actuatable outlet valve is used, does, however, have the great inherent disadvantage that drained condensate exits from the sterilizing container in a gush. Where sterilizing containers are stacked one on top of the other, the condensate can flow from the higher sterilizing container over the lid of the sterilizing container below it. This results in undesired cooling of the lower sterilizing container and in undesired subsequent formation of condensate in its container interior, which has to be additionally evaporated or drained. The through-opening in the bottom also proves to be particularly disadvantageous because the sterilizing container is inadequately sealed if the outlet valve is faulty or damaged. This may lead to unsatisfactory sterilization results and facilitate penetration of germs into the container interior. Especially when the through-opening is arranged in and the outlet valve on the bottom, there is a high risk that unevenesses of a set-down surface for the sterilizing container or objects placed on the set-down surface will act from below on the outlet valve and result in damage thereto or failure thereof. An uneven set-down surface or objects on the set-down surface may also cause the valve body to be lifted off from the valve seat of the outlet valve and the through-opening to be opened, and so even if the outlet valve is as such intact, there is a great risk of germs penetrating into the container interior. A further disadvantage is that owing to the through-opening being arranged in the bottom, it is difficult for hospital staff normally handling the sterilizing container to recognize failure of or damage to the outlet valve.

A sterilizing container of the kind described hereinabove with a through-opening in the bottom and an outlet valve arranged on the bottom is described, for example, in EP 1 035 873 B1.

"Set-down surface" is a surface on which the sterilizing container can be positioned. "Set-down plane" is a contact plane which is defined by the sterilizing container and in which the sterilizing container contacts the set-down surface. The horizontally aligned set-down surface, as is usually the case, will, when the sterilizing container is used in accordance with the specifications in an operating position, result in a horizontal alignment of the set-down or contact plane. Position and orientation details such as, for example, "at the top", "at the bottom" refer, in this case, to an operating position of the sterilizing container in which it is positioned in accordance with the specifications on a set-down surface.

An object underlying the present invention is to provide a surgical sterilizing container of the kind mentioned at the outset, from which it is possible to remove fluid which has formed in the container interior while reducing the risk of germs penetrating into the container interior.

SUMMARY OF THE INVENTION

In a first aspect of the invention, a surgical sterilizing container comprises a bottom and a container wall, a through-opening for the exchange of media being formed on the sterilizing container, and a valve device having an outlet valve for opening and closing the through-opening. The through-opening is formed in the container wall and is at a distance from the bottom, and the sterilizing container comprises a fluid lifting device for providing a fluid connection from the bottom to the outlet valve and for lifting fluid from the bottom to the outlet valve.

In a second aspect of the invention, a surgical fluid extraction device for use with a surgical sterilizing container having a container wall and a bottom comprises a valve device which has an outlet valve with which a through-opening formed in the container wall of the sterilizing container is openable and closable, and comprises a fluid lifting device for providing a fluid connection from the bottom to the outlet valve and for lifting fluid from the bottom to the outlet valve.

BRIEF DESCRIPTION OF THE DRAWINGS

The foregoing summary and the following description may be better understood in conjunction with the drawing figures. There are shown in.

DETAILED DESCRIPTION OF THE INVENTION

Figure 1:
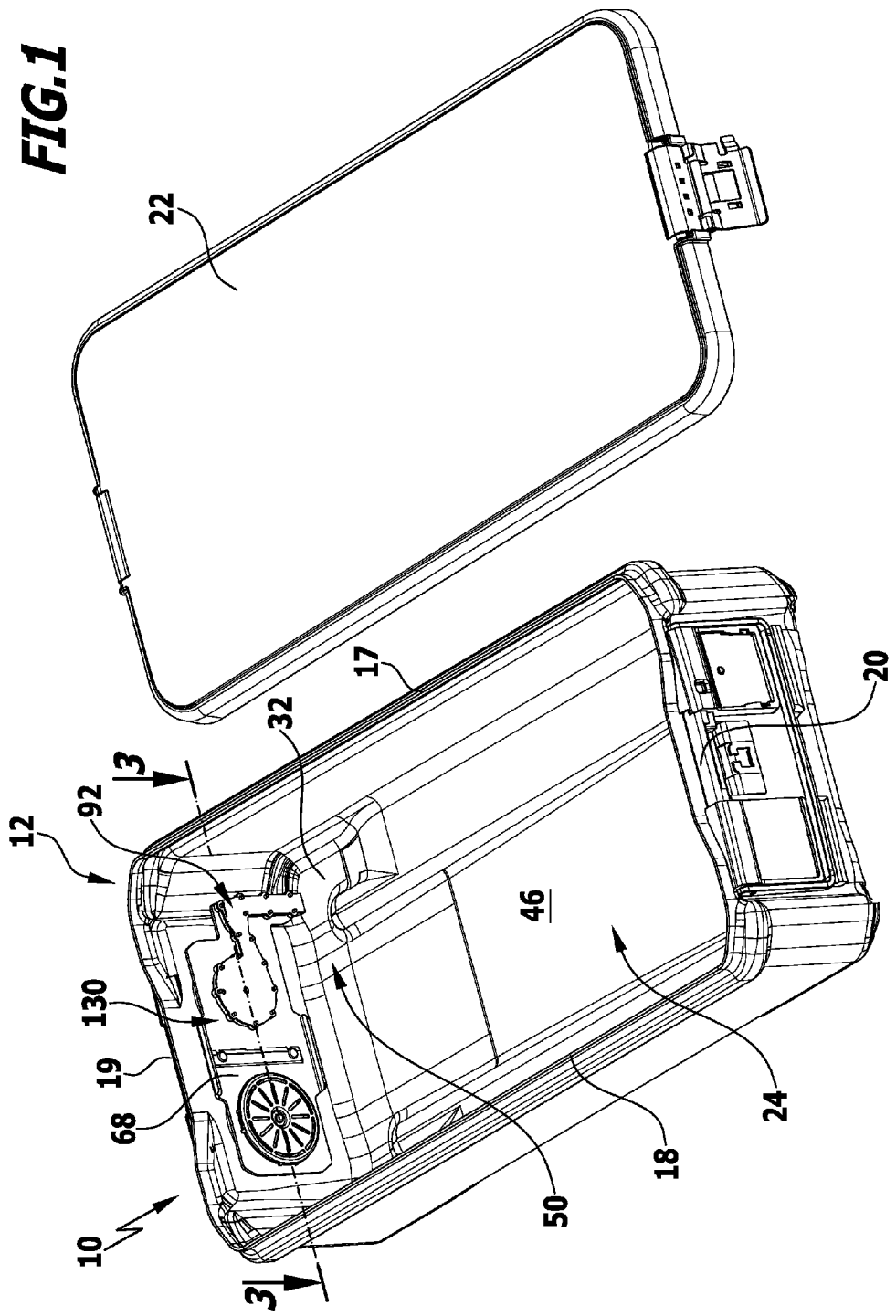
FIG. 1 a perspective representation of a sterilizing container in accordance with the invention in the open state, comprising a fluid extraction device in accordance with the invention.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical sterilizing container, comprising a bottom and a container wall, a through-opening for the exchange of media being formed on the sterilizing container, and comprising a valve device having an outlet valve for opening and closing the through-opening. The through-opening is formed in the container wall and is at a distance from the bottom, and the sterilizing container comprises a fluid lifting device for providing a fluid connection from the bottom to the outlet valve and for lifting fluid from the bottom to the outlet valve.

In the sterilizing container in accordance with the invention, the outlet valve is arranged at a distance from the bottom. The risk that an uneven set-down surface or objects placed on the set-down surface, as in the sterilizing container described hereinabove, will act on the outlet valve and open or damage it in an undesired manner can thereby be avoided to the greatest possible extent. This allows reliable functioning of the outlet valve for sealing the through-opening in the container wall in order to avoid penetration of germs into the container interior also after completion of the sterilization process. For removal of fluid from the container interior and, consequently, shortening of the drying phase, the sterilizing container in accordance with the invention comprises a fluid lifting device. The fluid lifting device forms a fluid connection from the bottom, where fluid such as, in particular, condensate, usually collects, and so fluid can be lifted by the fluid lifting device and conducted to the outlet valve. As a result, fluid can exit through the container wall, in particular, from the side of the sterilizing container. This makes it possible to avoid the aforementioned disadvantage of the known sterilizing container where fluid exits downwards from the sterilizing container in a gush. In the sterilizing container in accordance with the invention, it may, in particular, be provided that in addition to lifting fluid by means of the fluid lifting device and conducting it to the outlet valve, the internal pressure of the container can be reduced via a bypass path bypassing the fluid lifting device. This also makes it possible to reduce the mechanical load on the sterilizing container.

The bottom is preferably free of through-openings so that the bottom can form a sterile barrier of the sterilizing container. The disadvantages occurring in the conventional sterilizing container mentioned hereinabove owing to the through-opening in the bottom can thereby be avoided.

It is expedient if the sterilizing container comprises a sterilizing container tub including the bottom and having an outer wall projecting from the bottom. The outer wall forms a container wall of the sterilizing container. The container wall may also comprise a cover wall formed by a sterilizing container lid.

To achieve a constructionally simple design of the sterilizing container, it is expedient for the through-opening to be formed in the outer wall.

At least one further through-opening, for example, a through-opening which is openable and closable by an inlet valve of the valve device may be formed in the container wall. In a further through-opening a filter of the sterilizing container may be arranged, through which the exchange of media can take place between the container interior and the environment when the pressure differences are sufficiently low for neither the outlet valve nor the inlet valve to open. The through-openings in which the inlet valve and the filter are respectively arranged are preferably formed in the outer wall.

It may be provided that the sterilizing container tub is of rectangular or substantially rectangular cross section with four side walls forming the outer wall, and that the through-opening is formed in a side wall.

It proves advantageous in practice for the outer wall to comprise longitudinal side walls and transverse side walls and for the through-opening to be formed in one transverse side wall. There is, for example, formed next to the through-opening in the transverse side wall a further through-opening in which an inlet valve is arranged. In a transverse side wall opposite the transverse side wall there can be formed a through-opening in which a filter is arranged.

As mentioned above, the sterilizing container can comprise a sterilizing container lid. The lid can be adapted to be detachably fitted on a sterilizing container tub of the sterilizing container.

For a constructionally simple design and reliable functioning, the outlet valve is formed as a pressure relief valve which opens when a predetermined or predeterminable pressure difference prevails between the container interior and the environment and opens the through-opening. In addition to fluid, gas present in the container interior can exit through the outlet valve.

In order to also achieve a constructionally simple design, it is expedient if the fluid lifting device is pressure-actuatable and lifts fluid, for example, from the bottom in dependence upon the pressure difference between the container interior and the environment of the sterilizing container and conducts it to the outlet valve.

It is advantageous if the fluid lifting device comprises a fluid channel for providing the fluid connection, through which fluid is liftable from the bottom to the outlet valve and which comprises a channel inlet opening for fluid and a channel outlet opening for fluid arranged at a distance from the latter. Fluid can enter the fluid channel through the channel inlet opening which is preferably arranged on or near the bottom. Fluid can flow through the fluid channel and exit from the fluid channel through the outlet opening. The flow of fluid can be brought about, in particular, with the outlet valve open, by a suction flow prevailing in the fluid channel owing to the pressure difference between the ambient pressure and the pressure in the container interior. Fluid can thereby be drawn into the fluid channel, lifted and conducted to the outlet valve.

The channel inlet opening preferably faces in the direction of the bottom. This can, in particular, be understood as meaning that a direction opposite to the direction in which fluid passes into the fluid channel faces in the direction of the bottom. The lifting of fluid can thereby be simplified.

The channel inlet opening advantageously has an inclination relative to the bottom. This can, in particular, be understood as meaning that a rim of the fluid channel enclosing the inlet opening is inclined relative to the bottom. For example, the fluid channel has a slant at its end facing the bottom. With a predetermined fluid channel cross section, an enlarged fluid inlet opening can thereby be formed, which facilitates the lifting of fluid by drawing it in through the fluid channel.

The end of the fluid channel forming the fluid inlet opening is expediently arranged at a distance from the bottom in order to facilitate the drawing of fluid into the fluid channel.

It is expedient if the fluid channel with an end forming the channel inlet opening engages in a depression which is formed in the bottom and forms a fluid collection area for collecting fluid. Fluid such as, in particular, condensate, can be collected in the fluid collection area. Owing to the fluid channel engaging in the fluid collection area, an effective fluid connection from the fluid collection area to the outlet valve can be provided for lifting the fluid.

For example, the fluid collection area is arranged at a side wall of the sterilizing container tub, for example, at a transverse side wall and, in particular, at a corner area of the bottom, at which a transverse side wall and a longitudinal side wall of the sterilizing container tub converge.

The channel outlet opening is preferably directed at a valve body of the outlet valve. This can, in particular, be understood as meaning that the direction in which fluid passes through the channel outlet opening faces the valve body in order to effectively conduct fluid to the valve body.

For a constructionally simple design, it is advantageous if the channel outlet opening is directed at an upward flow side of the outlet valve, especially at the upward flow side of the valve body.

It is expedient if the channel outlet opening is arranged at a side of the outlet valve that faces the bottom in order to lift fluid over as short a distance as possible from the bottom.

It is advantageous if the fluid lifting device comprises an injector for lifting fluid through the fluid channel and if the injector comprises an injector inlet opening and an injector outlet opening, via which a flow connection is provided from a container interior defined by the sterilizing container to the outlet valve, and also an injector suction opening arranged in the direction of flow between the injector inlet opening and the injector outlet opening and formed by the fluid channel. An injector is provided in the fluid lifting device of this advantageous embodiment. A flow connection from the container interior to the outlet valve can be provided through the injector, from an injector inlet opening to an injector outlet opening. Owing to a pressure difference between the container interior and the environment of the sterilizing container, an effective suction flow can form through the injector with the outlet valve open. Between the injector inlet opening and the injector outlet opening, the injector has an injector suction opening which is formed by the fluid channel. Owing to the suction flow that forms, a pressure difference can arise at the fluid channel between the injector suction opening and the channel inlet opening located upstream in the direction of flow of the fluid through the fluid channel. This allows fluid to be lifted through the fluid channel and conducted to the outlet valve. It is found in practice that fluid can be effectively lifted and removed from the container in this way.

For constructional simplification, it is expedient if the injector is integrated in the fluid channel, the injector outlet opening preferably being formed by the channel outlet opening and/or the injector inlet opening being formed in a channel wall of the fluid channel. The injector inlet opening can, for example, be an inlet opening of the channel wall through which a bypass flow path is formed from the container interior to the outlet valve, bypassing the fluid channel from the channel inlet opening to the injector suction opening.

The injector can comprise, for example, downstream of the suction opening in the direction of flow, a diffuser, in order to calm the flow of fluid that has been drawn in and lifted. The diffuser can be integrated in the fluid channel.

It is advantageous, in particular, when an injector of the fluid lifting device is present, if the fluid channel has a cross-sectional constriction. This facilitates the formation of a pressure difference in the fluid channel in order to lift fluid from the bottom to the outlet valve. Downstream of the cross-sectional constriction, the fluid channel cross section can widen in order to form a diffuser.

It is advantageous if, in relation to the direction of flow of the fluid flowing from the bottom to the outlet valve, an inlet opening, via which a flow connection is provided from a container interior defined by the sterilizing container to the outlet valve, is formed upstream of the cross-sectional constriction in the fluid channel. The inlet opening is, in particular, the aforementioned injector inlet opening of the injector of the fluid lifting device.

In an advantageous embodiment of the sterilizing container in accordance with the invention, it is provided that the fluid channel has a first channel section aligned in a direction facing away from the bottom, and, in relation to the direction of flow of the fluid flowing from the bottom to the outlet valve, downstream of the first channel section, a second channel section which includes an angle with the first channel section. For example, the risk of lifted fluid exiting from the sterilizing container "in a burst of spray" can thereby be reduced.

The first channel section is expediently aligned at right angles or essentially at right angles to a set-down plane defined by the sterilizing container and can thereby face, in particular, vertically upwards from the bottom.

It proves to be advantageous if the second channel section has an inclination relative to a set-down plane defined by the sterilizing container. This can, in particular, be understood as meaning that the second channel section is inclined in the direction towards the set-down plane. Fluid lifted through the first channel section can flow in the fluid channel through the second channel section in the direction of the set-down plane again before reaching the outlet valve. The flow of fluid can thereby calm down so that fluid will not exit from the sterilizing container in a burst of spray.

For example, it may be provided that the first channel section and the second channel section include an angle of less than 90° with each other, for example, by the first channel section being aligned perpendicularly to the set-down plane and the second channel section being directed at the latter.

To achieve a constructionally simple and compact design, it proves to be advantageous if a section of the fluid channel is delimited by a channel wall formed by a valve holder on which the outlet valve is held and which is fixed to the container wall. The valve holder forms at least partially the channel wall of the fluid channel. For this purpose, the valve holder can have, for example, a groove-shaped or notch-shaped depression.

The fluid lifting device preferably comprises a channel wall which delimits at least a section of the fluid channel and forms a cover covering the outlet valve on the inner side of the container. This also allows a constructional simplification in which a channel wall can be simultaneously used to cover the outlet valve.

It proves expedient if at least one opening for forming a flow connection from a container interior defined by the sterilizing container to the outlet valve is provided in the cover. This makes it possible to reduce the pressure in the container interior while forming a bypass flow path and bypassing the fluid channel. Gas can flow through the at least one opening to the opened outlet valve and exit from the sterilizing container.

It may be provided that the outlet valve comprises a valve body which engages in at least one opening formed in the cover. The opening can thereby act as aligning element for the valve body. For example, the valve body has a pin-like projection which engages in the opening.

To achieve a constructionally simple design, it is advantageous if the cover is connected to the valve holder, and the fluid channel is formed between the cover and the valve holder. For this purpose, the valve holder preferably forms at least one channel wall of the fluid channel. There is, for example, provided in the valve holder a groove-shaped or notch-shaped depression which is covered by the cover.

It is expedient if the fluid channel is of dimensionally stable construction. This allows a robust construction of the fluid channel which does not undergo deformation, in particular, even when high pressures prevail in the container interior. This also facilitates a reliable functioning of the fluid lifting device.

To achieve a compact construction, the fluid channel can, for example, be fixed to a side wall of the sterilizing container, it being possible for it to be indirectly or directly fixed to the side wall. For example, the fluid channel is fixed to the valve holder or partially formed by the latter, which is fixed to a side wall and, in particular, a transverse side wall of the sterilizing container.

To achieve a compact construction, the fluid channel preferably extends parallel to a side wall and, in particular, a transverse side wall of the sterilizing container.

The fluid lifting device can, for example, be completely or partly arranged laterally next to the outlet valve, also in order to achieve a compact construction.

To obtain the same advantage, it may be provided that the fluid lifting device is completely or partly arranged below the outlet valve. For example, the fluid lifting device is arranged between the bottom and the outlet valve.

As mentioned above, the sterilizing container can comprise a valve holder on which the outlet valve is held and which is fixed to the container wall, for example, to a transverse side wall of the sterilizing container. This makes it possible, depending on sterilizing container and/or sterilization process requirements, to provide different valve holders with different outlet valves and/or fluid lifting devices arranged thereon, which can be connected, as required, to the respective container wall.

The valve holder is preferably detachably fixed to the container wall so that it can be detached from the latter and exchanged as required. The attachment is effected, for example, by latching and/or clamping.

The valve holder is advantageously inserted in the through-opening and forms a valve seat of the outlet valve. The valve holder can lie sealingly against the container wall and engage in the through-opening in the container wall. In order to achieve a constructional simplification, the valve seat of the outlet valve can be formed by the valve holder. The through-opening formed in the container wall, insofar as it is not covered by the valve holder itself, can be closed and opened by the outlet valve.

The valve holder is preferably plate-shaped or substantially plate-shaped in order to achieve a constructionally simple design.

As mentioned above, the sterilizing container can comprise an inlet valve. For example, a further through-opening can be formed in the container wall, with the valve device comprising an inlet valve for opening and closing the further through-opening.

To achieve a constructionally simple design, it is expedient if the valve device comprises an inlet valve which is held on the valve holder. It may also be provided that a double-acting outlet and inlet valve is provided.

The present invention further relates to a fluid extraction device for use with a surgical sterilizing container having a container wall and a bottom. The fluid extraction device for extracting fluid from the sterilizing container comprises a valve device which has an outlet valve with which a through-opening formed in the container wall of the sterilizing container is openable and closable, and comprises a fluid lifting device for providing a fluid connection from the bottom to the outlet valve and for lifting fluid from the bottom to the outlet valve.

The advantages mentioned in the context of the explanation of the sterilizing container in accordance with the invention can be achieved when the fluid extraction device in accordance with the invention is used in accordance with the specifications with the sterilizing container. In this connection, reference is made to the explanations given above.

Features of the sterilizing container in accordance with the invention relating to the valve device and the fluid lifting device and also advantageous embodiments of the sterilizing container can also be provided for the valve device and the fluid lifting device of the fluid extraction device in accordance with the invention. In this connection, reference can be had to the foregoing explanations in which these features were mentioned together with the advantages achievable with them in each case. These features can be used to form advantageous embodiments of the fluid extraction device in accordance with the invention. In particular, the fluid lifting device of the fluid extraction device in accordance with invention can comprise the aforementioned fluid channel and the aforementioned injector including their respective features, the injector preferably being integrated in the fluid channel. The injector can comprise the diffuser which can be integrated in the fluid channel. Furthermore, it is expediently provided that the fluid extraction device comprises a preferably one-piece valve holder, on which the outlet valve is held, and which is preferably detachably fixable to the container wall, and that the fluid lifting device is arranged on the valve holder, for example, is connected to it, is connectable to it or is partly formed by it. For example, a channel wall of the fluid channel can be formed by the valve holder. A channel wall of the fluid channel can form a cover of the outlet valve. The fluid channel can be formed between the valve holder and the cover. The fluid channel can comprise channel sections aligned at an angle, for example, of less than 90°, to each other. The valve holder can form the valve seat of the outlet valve and/or, if provided, of the inlet valve.

FIG. 1 shows in perspective representation a preferred embodiment, denoted in its entirety by reference numeral 10, of a sterilizing container in accordance with the invention. The sterilizing container 10 serves to hold surgical instruments during the sterilization process. The instruments, not shown in the drawings, are usually arranged in a receptacle, not shown in the drawings either, for example, in a surgical screen basket held in the sterilizing container 10.

The sterilizing container 10 comprises a sterilizing container tub 12 of generally rectangular shape, which has a bottom 14 and an outer wall 16 protruding from the bottom 14. The bottom 14 is formed by a bottom wall 15. The outer wall 16 comprises four side walls, namely two longitudinal side walls 17 and 18, which are joined to each other at the ends by two transverse side walls 19 and 20, respectively. The outer wall 16 is a container wall of the sterilizing container 10. The longitudinal side walls 17 and 18 define a longitudinal direction of the sterilizing container 10. The transverse side walls 19 and 20 define its transverse direction.

The sterilizing container 10 comprises a sterilizing container lid 22, which can be fitted sealingly on the sterilizing container tub 12 in order to cover it and close a container interior 24 defined by sterilizing container 10. The sterilizing container lid 22 can be detachably connected to the sterilizing container tub 12 by closure elements known per se.

The sterilizing container tub 12 defines a set-down plane 26 of the sterilizing container 10, which is a contact plane in which the sterilizing container tub 12 contacts a set-down surface on which it is set down. Where a set-down surface is aligned horizontally, as is usually the case, the set-down plane 26 is aligned horizontally.

Position and orientation details such as, for example, "at the top", "at the bottom" or the like relate in this context to a position of use of the sterilizing container 10 on a horizontal set-down surface and hence on a horizontally aligned set-down plane 26 in an operating position of the sterilizing container 10.

Figure 4:
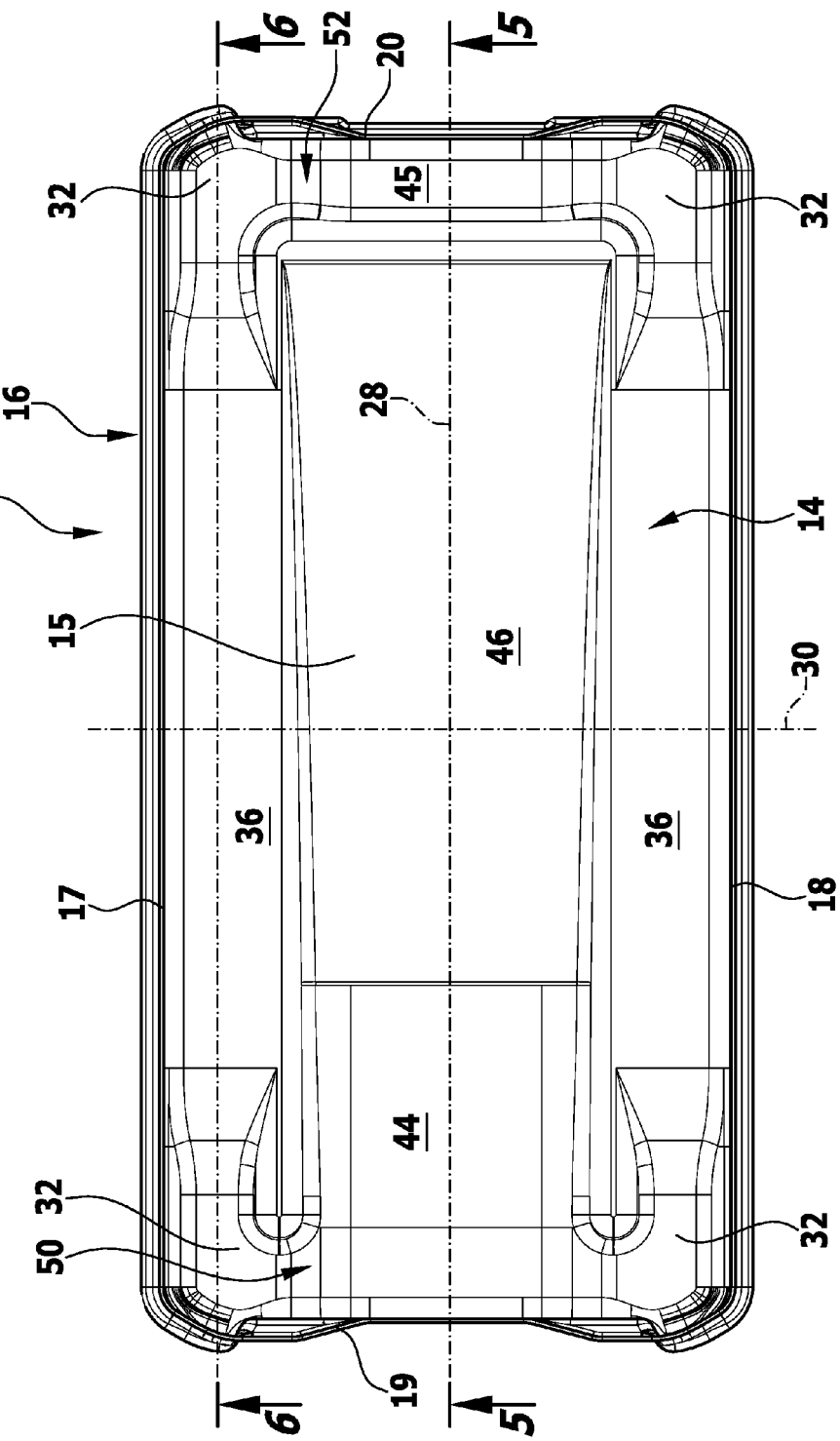
FIG. 4 a plan view of a sterilizing container tub of the sterilizing container from FIG. 1.

The sterilizing container tub 12, especially the bottom 14, is overall of symmetrical configuration in relation to a plane of symmetry 28, which is aligned perpendicularly to the set-down plane 26 and is a center plane of the tub. The plane of symmetry 28 runs centrally between the longitudinal side walls 17 and 18, in FIG. 4 perpendicularly to the plane of drawing and along line 5-5.

Furthermore, the sterilizing container tub 12, especially the bottom 14, is of asymmetrical configuration in relation to a plane of asymmetry 30, which is aligned perpendicularly to the set-down plane 26 and perpendicularly to the plane of symmetry 28 and which is a center plane of the tub, which runs centrally between the transverse side walls 19 and 20.

In corner areas of the sterilizing container tub 12 where the longitudinal side walls 17, 18 and the transverse side walls 19, 20 meet one another there are depressions 32 in the bottom 14. The depressions 32, like the remaining bottom 14, are formed during the forming of the sterilizing container tub 12 by a forming process, for example, by deep drawing. Due to formation of the depressions 32, the bottom 14 has set-down elements 34 on the outside, which define the set-down plane 26.

The sections of the bottom wall 15 in the area of depressions 32 located opposite each other in the longitudinal direction are connected to each other by bottom sections 36 which extend along the longitudinal side walls 17 and 18. The bottom sections 36 extend in the longitudinal direction over approximately 60% of the length and in the transverse direction over approximately 25% of the bottom 14. The bottom sections 36 are of planar configuration and form supporting elements 38 which define a supporting plane 40 aligned parallel to the set-down plane 26. No sections of the bottom wall 14 extend beyond the supporting plane 40. A receptacle for surgical instruments, in particular, a surgical screen basket, can be reliably placed in an upright position on the supporting elements 38.

In the transverse direction, the bottom sections in the area of the depressions 32 are connected to each other along the transverse side wall 19 by a bottom section 44. Along the transverse side wall 20, the bottom sections in the area of the depressions 32 are connected to each other by a bottom section 45.

Figure 5:
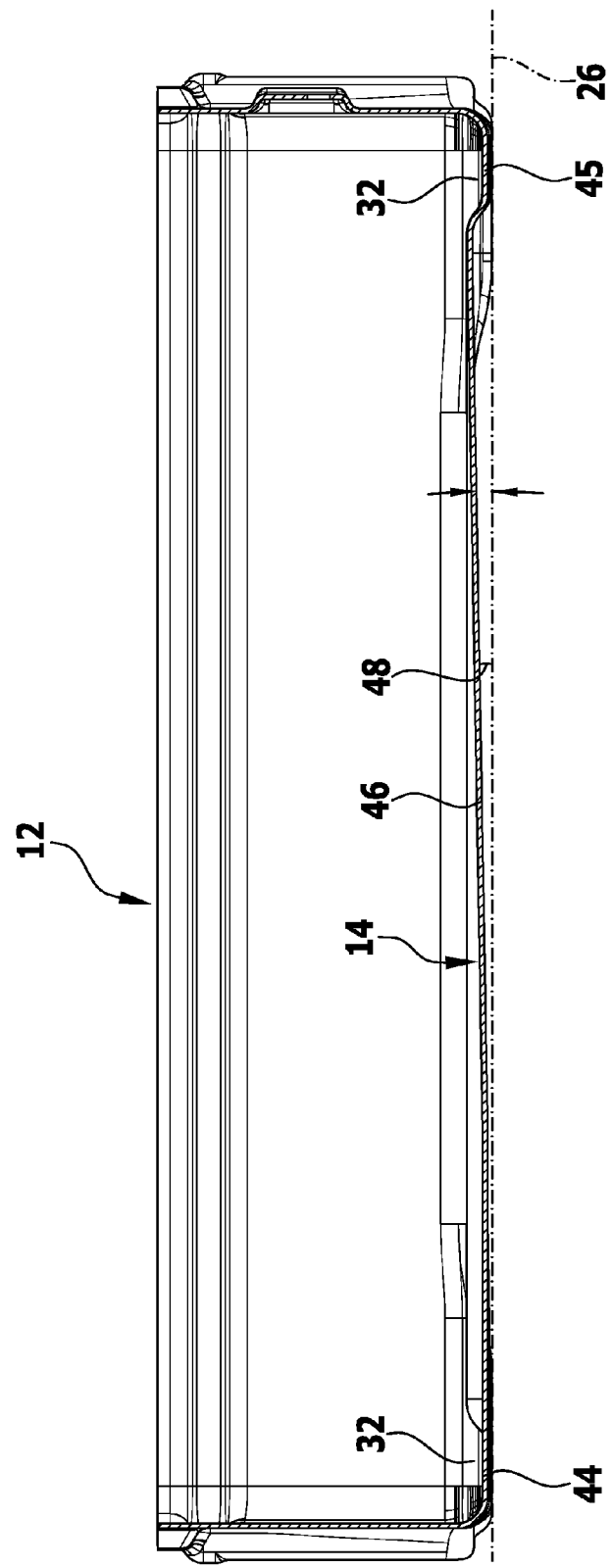
FIG. 5 a sectional view along line 5-5 in FIG. 4.
Figure 6:
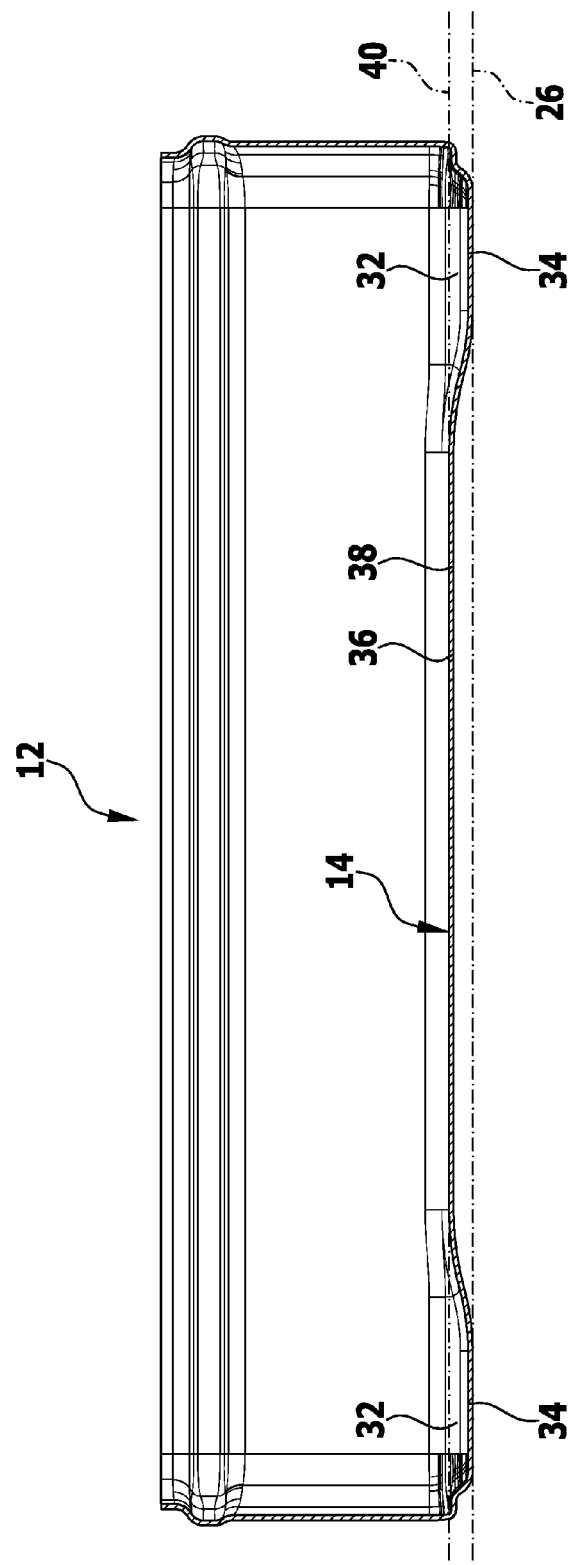
FIG. 6 a sectional view along line 6-6 in FIG. 4.

The bottom sections 44 and 45 define a common plane which is aligned parallel to the set-down plane 26 and is at a shorter distance from it than from the supporting plane 40 (FIG. 5). The bottom section 44 extends in the longitudinal direction over an area of approximately one quarter of the length of the bottom 14, the bottom section 45 over approximately 10% of the length of the bottom 14. At a distance from the transverse side wall 19, the bottom section 44 is connected to a fluid drainage surface 46 of the bottom 14, the connection being effected in the transverse direction of the bottom 14.

The fluid drainage surface 46 extends in the longitudinal direction from the bottom section 44 to the bottom section 45 and in the transverse direction between the bottom sections 36. The fluid drainage surface 46 thereby covers the center of the bottom 14 through which the plane of symmetry 28 and the plane of asymmetry 30 run. The fluid drainage surface 46 is of planar configuration and, in a plan view of the sterilizing container tub 12, is approximately trapezoidal with a base facing the transverse side wall 20. On the side opposite the base, the fluid drainage surface 46 is connected to the bottom section 44. All in all, the fluid drainage surface 46 extends over approximately one third of the surface of the bottom 14.

It thereby covers approximately 60% to approximately 70% of the bottom surface in the longitudinal direction and approximately 50% of the bottom surface in the transverse direction.

The fluid drainage surface 46, in particular, the plane defined by it, is inclined at an angle of inclination 48 relative to the set-down plane 26. The fluid drainage surface 46 does not intersect the set-down plane as it only extends as far as the bottom section 44 in the direction of the set-down plane. The angle of inclination 48 is, in this case, less than 2°, for example, approximately 1.5°. The fluid drainage surface 46 is inclined in the direction of the transverse side wall 19 so that at its end facing the transverse side wall 19 it is at a shorter distance from the set-down plane 26 than at its end opposite the transverse side wall 19. The latter end starts from the supporting plane 40, and the end of the fluid drainage surface 46 that faces the side wall 19 is arranged in the plane defined by the bottom section 44.

The inclination of the fluid drainage surface 46 has the consequence that fluid, in particular, condensate formed during the sterilization process, is drained off from the fluid drainage surface 46 in the direction of the transverse side wall 19. Since the bottom section 44 and the bottom wall 15 in the area of the depressions 32 at the transverse side wall 19 are at a shorter distance from the set-down plane 26 than the fluid drainage surface 46 (apart from its connection with the bottom section 44) fluid is conducted to the bottom section 44 and the depressions 32 at the transverse side wall 19. The bottom 14 in the area of the bottom section 44 and of the depressions 32 at the transverse side wall 19 thereby forms a fluid collection area 50. Fluid drained off from the fluid drainage surface 46 collects in the fluid collection area 50, with fluid first being drained off into the depressions 32 at the transverse side wall 19. As the fluid level rises, fluid can also collect on the bottom section 44 which lies somewhat higher in relation to the bottom wall 15 in the area of the depressions 32.

In the configuration mentioned above, the fluid collection area 50 extends along the transverse side wall 19 which delimits a section of the fluid collection area 50 at the transition to the bottom wall 15. The fluid collection area 50 is, therefore, adjacent to the transverse side wall 19. Fluid can also be conducted from the bottom sections 36 in the longitudinal direction via slants of the bottom wall 15 into the depressions 32 at the transverse side wall 19.

The bottom 14 has a further fluid collection area 52 along the transverse side wall 20. The fluid collection area 52 is formed by the depressions 32 at the transverse side wall 20 and by the area lying between these in the transverse direction and delimited at the bottom by the bottom section 45. Fluid can also be drained off from the bottom sections 36 into the depressions 32 at the transverse side wall 20. However, the total amount of fluid collecting in the fluid collection area 52 is substantially less than the amount of fluid collecting in the fluid collection area 50. This is due to the asymmetrical configuration of the bottom 14 relative to the plane of asymmetry 30 and the inclined fluid drainage surface 46 by which the predominant amount of fluid is drained off in the direction of the transverse side wall 19 into the fluid collection area 50.

Three through-openings are provided in the outer wall 16 to enable an exchange of media such as gas and/or fluid from the container interior 24 to the environment and conversely also when the sterilizing container 10 is closed. In contrast, the cover wall of the sterilizing container lid 22 and the bottom 14 are free of openings.

Figure 7:
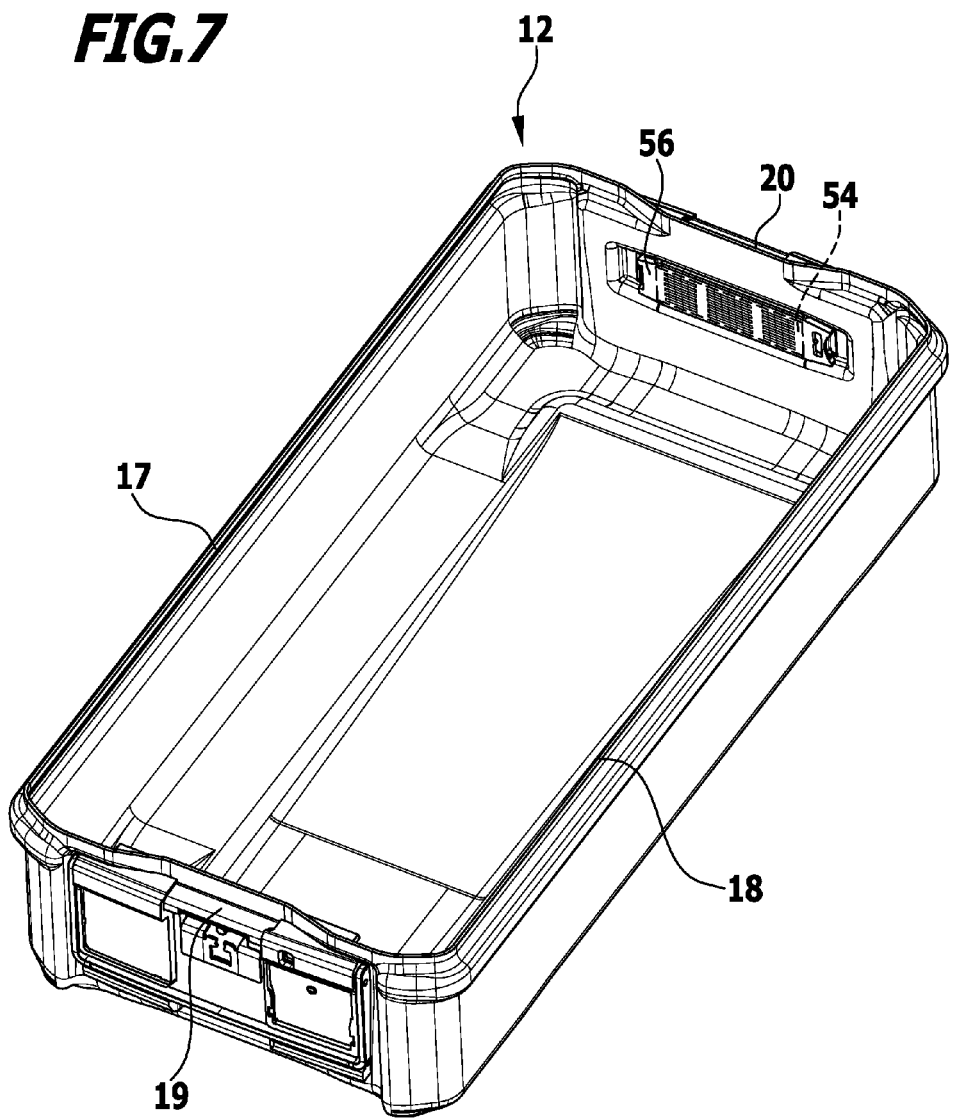
FIG. 7 a perspective representation of a sterilizing container tub of the sterilizing container from FIG. 1.

A first through-opening, not shown in the drawings, is formed in the transverse side wall 20. The through-opening is covered (FIG. 7) by a filter 54. The filter 54 is held by a filter retaining element 56 in the form of a retaining plate on the transverse side wall 20, thereby covering the through-opening. An exchange of media takes place between the environment and the container interior 24 through the filter 54 provided a first maximum pressure difference between the environment and the container interior is not exceeded or a second maximum pressure difference between the container interior 24 and the environment is not exceeded.

To enable an exchange of media in the latter cases and to avoid damage to the filter 54, the sterilizing container 10 comprises a valve device 58. The valve device 58 serves to open and close two through-openings 60 and 62 which are formed laterally next to each other in the transverse side wall 19 and at a distance from the bottom 14. In this case, the through-openings 60 are circular. The valve device 58 comprises an inlet valve 64 and an outlet valve 66, respectively, for closing and opening the through-openings 60 and 62.

Figure 3:
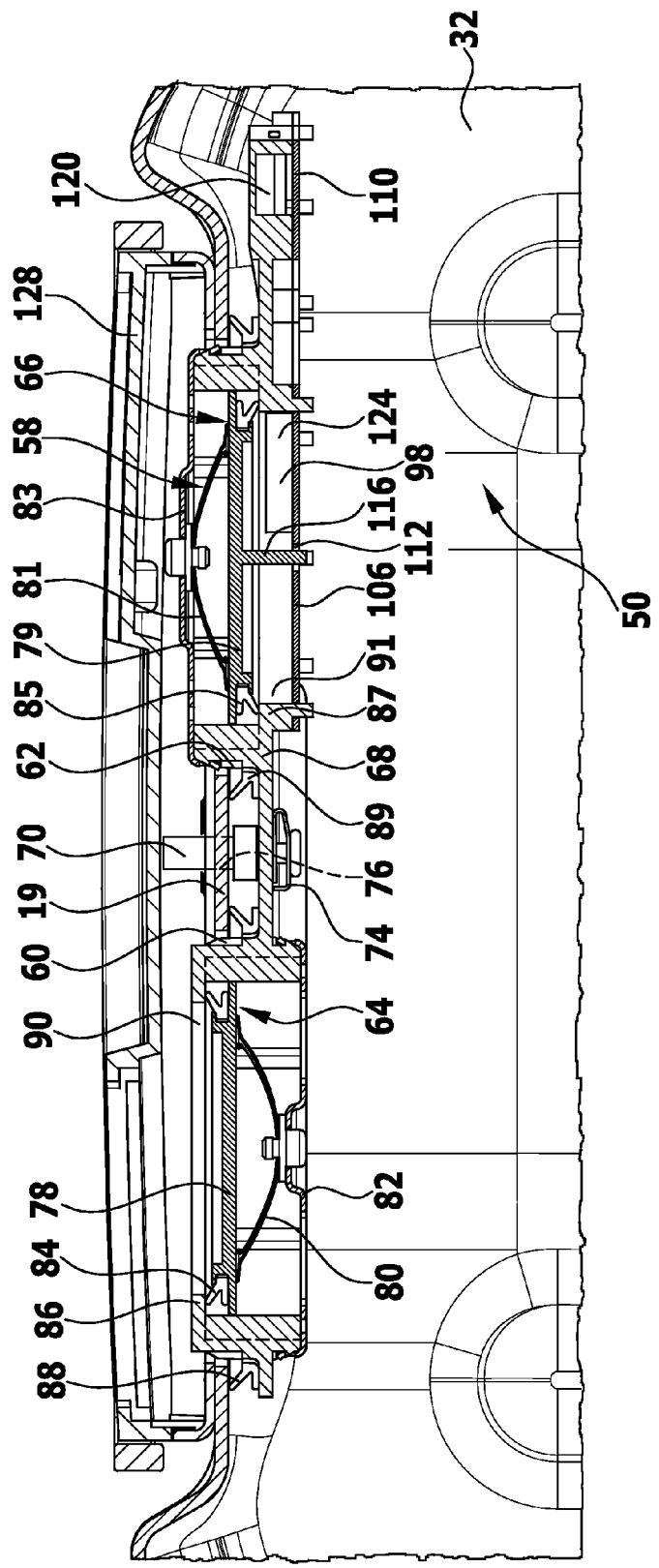
FIG. 3 a sectional view along line 3-3 in FIG. 1.

Associated with the valves 64 and 66 is a valve holder 68, in this case, of one-piece construction, on which the valves 64 and 66 are held. The valve holder 68 is of substantially plate-shaped configuration and is detachably connected to the transverse side wall 19. Connecting elements in the form of rivets (one rivet 70 is shown in FIG. 3) are provided for this purpose. The rivet 70 passes through a through-hole 72 in the valve holder 68 relative to which it is fixed in a force-locked and positively locked manner by a clamping element 74. The clamping element 74 is configured as a clamping rail by means of which both rivets can be fixed to the valve holder 68. With its free end, the rivet 70 passes through a through-hole 76 in the transverse side wall 19. The rivet 70 is in force-locked and positively locked engagement with the rim of the through-hole 76 so that it is thereby fixed to the transverse side wall 19.

To release the valve holder 68 from the transverse side wall 19, the force-locked engagement of the rivet with the clamping element 74 can be deactivated and the valve holder 68 with the valves 64 and 66 released from the sterilizing container tub 12. Conversely, the valve holder 68 can be connected to the sterilizing container tub 12 and fixed to it with the clamping element 74.

The inlet valve 64 and the outlet valve 66 are pressure-actuated valves with disk-shaped valve bodies 78 and 79, respectively, which are supported by elastic reset elements 80 and 81, respectively, in the form of yoke springs on media-permeable valve covers 82 and 83, respectively, which are connected to the valve holder 68. By means of sealing elements 84 and 85, respectively, in this case, in the form of lip seals, the valve bodies 78 and 79, respectively, can lie sealingly against valve seats 86 and 87, respectively, of the inlet valve 64 and the outlet valve 66, respectively. The valve seats 86 and 87 are formed by the valve holder 68. Via sealing elements 88 and 89, respectively, in this case, also in the form of lip seals, which extend around the rims of the through-openings 60 and 62, the valve holder is inserted sealingly into the through-openings 60 and 62. The valve holder 68 thereby reduces the cross-sectional area of the through-openings 60 and 62. When mention is made herein of opening and closing the through-openings 60 and 62 by the inlet valve 62 and the outlet valve 66, respectively, this refers to through-openings 90 and 91, respectively, in the valve holder 68, the rims of which are inserted into the through-openings 60 and 62 so that the cross sections of the through-openings 90 and 91 are smaller than those of the through-openings 60 and 62, respectively.

The sterilizing container 10 in accordance with the invention comprises a fluid lifting device 92 for lifting fluid out of the fluid collection area 50 and conducting it to the outlet valve 66. Fluid, in particular, condensate formed during the sterilization process, can be collected in the fluid collection area 50, in particular, in the depression 32 in the area of the transverse side wall 19 and the longitudinal side wall 17. The fluid lifting device 92 establishes a fluid connection between the fluid collection area 50 and the outlet valve 66 in order to remove fluid from the container interior 24.

For this purpose, the fluid lifting device 92 comprises a fluid channel 94 with a channel inlet opening 96 and a channel outlet opening 98. The fluid channel 94 comprises a first channel section 100 forming the channel inlet opening 96 and a second channel section 102 forming the channel outlet opening 98.

Figure 2:
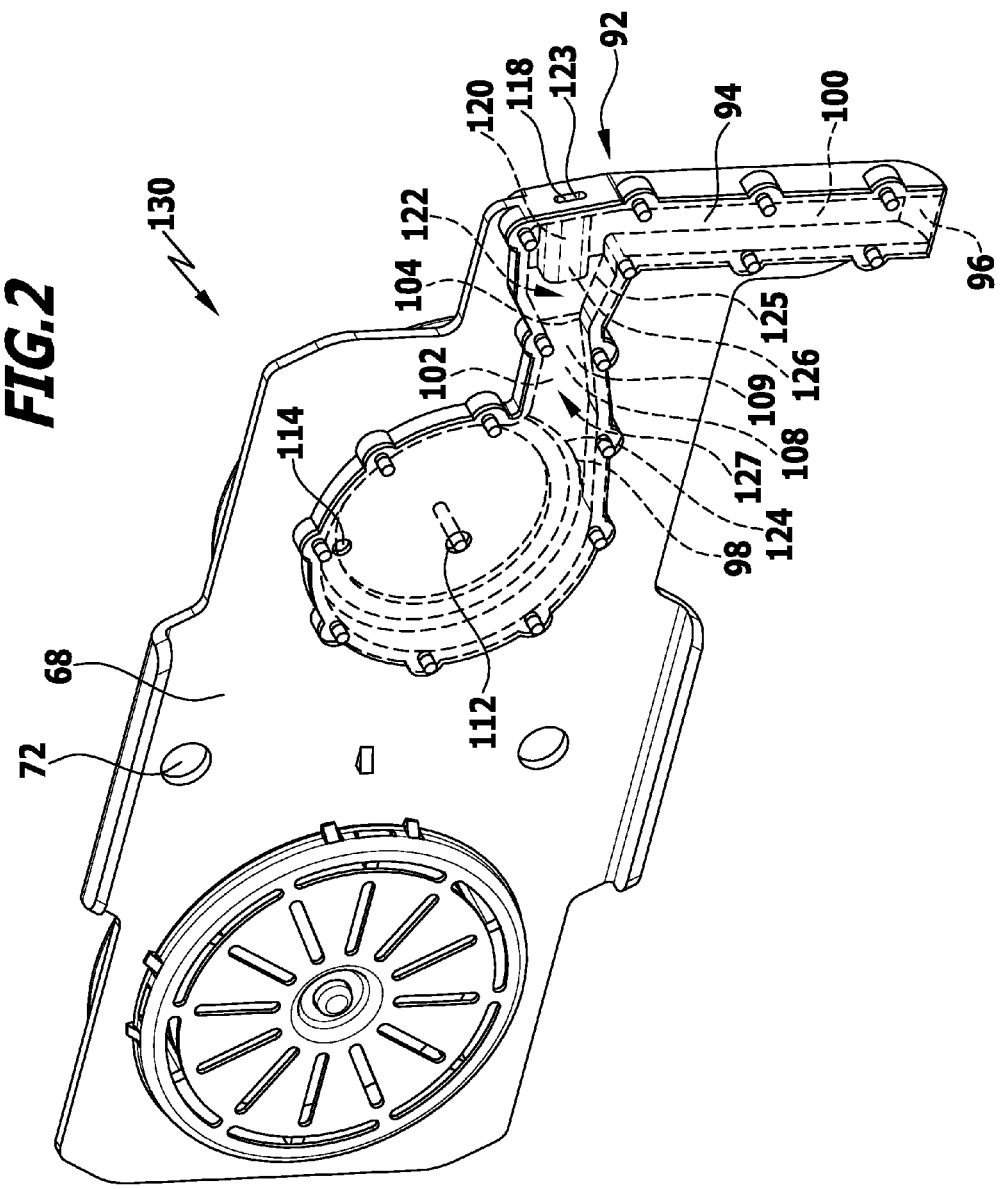
FIG. 2 a perspective representation of the fluid extraction device of the sterilizing container from FIG. 1.

The first channel section 100 engages into the depression 32 in the corner area of the transverse side wall 19 with the longitudinal side wall 17 and, therefore, into the fluid collection area 50, but it does not contact the bottom wall 15. The distance of the channel section 100 from the bottom wall is, for example, approximately 1 to 5 mm. The first channel section 100 is perpendicularly aligned relative to the set-down plane 26 and extends from it pointing upwards to approximately half of the height of the transverse side wall 19. The channel inlet opening 96 is directed at the bottom wall 15, which can be understood as meaning that the direction opposite to the direction of passage of fluid through the channel inlet opening 96 faces the bottom wall 15 (FIG. 1). The inlet opening 96 has an inclination in relation to the bottom wall 15 owing to a slant of the first channel section 100 at the end facing the bottom wall 15 (FIG. 2).

The second channel section 102 and the first channel section 100 are aligned at an angle relative to each other, which, in this case, is less than 90°. A direction defined by the second channel section 102 is inclined relative to the set-down plane 26, so that the second channel section 102 slopes down in the direction of the set-down plane 26. The channel outlet opening 98 is arranged at a side of the outlet valve 66 facing the bottom 14. The channel outlet opening 98 is directed at the upward flow side of the outlet valve 66, the direction of passage of fluid through the channel outlet opening 98 being substantially parallel to a plane defined by the disk-shaped valve body 79. The second channel section 102 has a channel constriction 104 in the region of which the cross-sectional area of the fluid channel 94 is reduced in size. Downstream in the direction of flow of the fluid through the fluid channel 94, the cross section of the fluid channel 94 widens again after the channel constriction 104 up to the channel outlet opening 98.

The fluid channel 94 is formed by channel walls, which are formed by the valve holder 68 and a cover 106 connected thereto. For this purpose, there is formed in the valve holder 68 a groove 108 which forms a first channel wall 109 of the fluid channel 94. The channel wall 110 located opposite the channel wall 109 is formed by the cover 106. The channel walls 109 and 110 are formed by lateral groove walls of the groove 108 of the valve holder 68.

The cover 106 covers the groove 108 and the through-opening 91 in the valve holder 68 and, therefore, the outlet valve 66 on the inner side of the container. Owing to the aforementioned configuration, the fluid channel 94 extends between the valve holder 68 and the cover 106 which, in this case, is plate-shaped, substantially in a or parallel to a plane defined by the valve holder 68.

Owing to the rigid configuration of the valve holder 68 and the cover 106, the fluid channel 94 is dimensionally stable. The fluid channel 94 is detachably connected to the transverse side wall 19 via the valve holder 68.

In its section covering the through-opening 91, the cover 106 has two through-holes 112 and 114. A projection 116, in this case pin-shaped, on the valve body 79 engages in the central through-hole 112 when the outlet valve 66 is closed. The projection 116 and the through-hole 112 therefore serve as interacting aligning elements for aligning the valve body 79 relative to the cover 106. The through-hole 114 is arranged above the through-hole 112 and is located opposite the outer rim of the valve body 79 on the inner side of the container.

In the area of transition from the first channel section 100 to the second channel section 102, the fluid channel 94 has an inlet opening 118, in an extension of the direction defined by the second channel section 102. A sleeve-shaped insert 120, the passage of which is in alignment with the inlet opening 118, is arranged in the fluid channel 94, in the area in which the second channel section 102 branches off from the first channel section 100. The insert 120 and, consequently, the inlet opening 118 of the channel constriction 104 are located upstream in relation to the direction of flow of fluid through the fluid channel 94.

The fluid lifting device 92 comprises an injector 122 integrated in the fluid channel 94 and having an injector inlet opening 123, an injector outlet opening 124 and a suction opening 125. The injector inlet opening 123 is formed by the inlet opening 118 of the fluid channel 94, and the injector outlet opening 124 is formed by the channel outlet opening 98. The suction opening 125 is formed by the fluid channel 94 in its area surrounding the insert 120. The insert 120 has the function of a nozzle 126 of the injector 122. The injector further comprises a diffuser 127 which is integrated in the channel and a section of which is formed by the second channel section 102. The diffuser 127 extends from the channel constriction 104 to the channel outlet opening 98.

The purpose and function of the fluid lifting device 92 in combination with the outlet valve 66 are discussed in detail hereinbelow. The fluid lifting device 92 is provided in order to remove liquid, in particular, condensate, from the container interior 24 at the end of the sterilization process. The ambient pressure around the sterilizing container 10 is reduced until it is significantly below the internal pressure of the sterilizing container 10. Owing to the pressure difference, the pressure-controlled outlet valve 66 opens so that a pressure compensation with the ambient pressure can take place. Gas and fluid can exit from the sterilizing container 10.

To open the outlet valve 66, it proves to be advantageous that flow connections between the outlet valve 66 and the container interior 24 are formed by the through-holes 112 and 114 of the cover 106 and by the inlet opening 118 in the fluid channel 94, thereby bypassing the first channel section 100 when there is a sufficiently high level of condensate in the depression 32. Owing to the elevated internal pressure of the container, bypass flow paths circumventing the first channel section 100 can form through the inlet opening 118 and the second channel section 102 and also through the through-holes 112 and 114 when the outlet valve 66 is opened.

Depending on the height of the level of condensate in the fluid collection area 50, it is, however, also possible that a flow of gas will form through the first channel section 100 if the condensate level is so low that the first channel section 100 with the channel inlet opening 96 is not fully immersed in fluid.

When the outlet valve 66 opens, a suction flow is generated through the injector 122 by gas flowing through the inlet opening 118 and the nozzle 126 and through the second channel section 102 to the outlet valve 66. Owing to the channel constriction 104, a reduction in pressure occurs at the suction opening 125, and so a pressure difference forms in the fluid channel 94 between the suction opening 125 and the pressure at the channel inlet opening 96. This results in fluid being drawn out of the fluid collection area into the fluid channel 94. Fluid is then lifted further through the fluid channel 94 and conducted to the outlet valve 66, under constant suction flow through the injector 122.

Here it proves to be advantageous that the second channel section 102 is inclined in the direction of the set-down plane 26. This results in the flow of lifted fluid calming down and so after leaving the fluid channel 94 it does not exit from the sterilizing container 10 in a burst of spray. For this purpose, the diffuser 127 is also provided between the channel constriction 104 and the channel outlet opening 98 to ensure an increase in pressure and, at the same time, a calming of the flow of the fluid. Also, for protection against spraying of exiting fluid, a substantially plate-shaped cover element 128 is held on the outer side of the transverse side wall 19. The cover element 128 also serves to accommodate and mount a container handle of the sterilizing container 10.

The lifting of fluid out of the fluid collection area 50 through the fluid channel 94 under the action of the suction flow through the injector 122 is also possible and effective when the fluid level has dropped so far that the first channel section 100 is not completely immersed with the channel inlet opening 96 in the fluid. Even with a mixed flow of condensate and gas through the first channel section 100, it is found that under the action of the suction flow through the injector 122, fluid can continue to be lifted effectively out of the fluid collection area 50 and conducted to the outlet valve 66.

Furthermore, it proves to be advantageous, in particular, with a high level of condensate rising above the channel inlet opening 96, that bypass flow paths circumventing the first channel section 100 are present through the through-holes 112 and 114 and the inlet opening 118. This results in a pressure drop in the container interior 24 over more than only one flow path, and so fluid is not drawn off through the fluid channel 94 and removed from the sterilizing container 10 in a gush. Also the mechanical load on the sterilizing container 10 can be thereby reduced.

After closing the outlet valve 66, fluid that may still be present in the sterilizing container 10 can evaporate during the drying phase following the actual sterilization process due to the residual heat especially of the sterilizing container tub 12 and exit from the container interior 24 through the filter 54. In this connection, it proves to be advantageous that the fluid collection area 50 extends along the transverse side wall 19 so that the residual heat stored in the transverse side wall 19 is also effective for evaporating fluid. The same applies to the fluid collection area 52 which extends along the transverse side wall 20.

The provision of the fluid lifting device 92 proves to be advantageous for effectively lifting a large amount of fluid and removing it from the container interior 24 even before the actual drying phase of the sterilization process starts. The drying phase can thereby be considerably shortened.

Furthermore, it is particularly expedient that the bottom 14 is free of any through-openings. Valves for closing the bottom 14 can thereby be dispensed with, and the bottom 14 forms a sterile barrier. The risk of germs entering by way of through-openings in the bottom, as is the case with sterilizing containers having fluid draining valves in the bottom, can thereby be avoided also after completion of the sterilization process. Damage to or malfunction of a fluid draining valve can also be prevented.

The outlet valve 66 and the fluid lifting device 92 are, in this case, part of a preferred embodiment of a surgical fluid extraction device in accordance with the invention, shown perspectively in FIG. 2 and denoted by reference numeral 130, which is used in the sterilizing container 10. The fluid extraction device 130 further comprises the valve holder 68 and the inlet valve 64. It may alternatively be provided that the inlet valve 64 is not held in the valve holder 68 and, consequently, is not part of the fluid extraction device 130. As mentioned, the fluid extraction device 130 can be detachably connected to the transverse side wall 19 which, in addition to facilitating assembly, also enables it to be exchanged when required.

What is claimed is:

1. Surgical sterilizing container, comprising:
    a bottom and a container wall,
    a through-opening for exchange of media being formed on the sterilizing container,
    a valve device comprising a pressure-actuatable outlet valve for opening and closing the through-opening, the through-opening being formed in the container wall and being at a distance from the bottom,
    a fluid lifting device for providing a fluid connection from the bottom to the outlet valve, the fluid lifting device comprising a fluid channel for providing the fluid connection, through which fluid is liftable from the bottom to the outlet valve and comprising a channel inlet opening for the fluid and a channel outlet opening for the fluid, and
    a valve holder, which is fixed to the container wall, on which the outlet valve is held,
    wherein:
    the valve holder is fixed to the container wall from an inner side of the container,
    the valve holder is inserted in the through-opening and forms a valve seat of the outlet valve,
    the fluid channel is delimited by at least a first channel wall formed by the valve holder and a second channel wall which forms a cover covering the outlet valve on the inner side of the container.

2. Sterilizing container in accordance with claim 1, wherein the bottom is free of through-openings.

3. Sterilizing container in accordance with claim 1, further comprising a sterilizing container tub which comprised the bottom and an outer wall projecting from the bottom.

4. Sterilizing container in accordance with claim 3, wherein:
    the sterilizing container tub is of rectangular or substantially rectangular cross section with four side walls forming the outer wall, and
    the through-opening is formed in a side wall.

5. Sterilizing container in accordance with claim 1, wherein the fluid lifting device is pressure-actuatable.

6. Sterilizing container in accordance with claim 1, wherein the channel inlet opening faces in a direction of the bottom.

7. Sterilizing container in accordance with claim 1, wherein the channel inlet opening has an inclination relative to the bottom.

8. Sterilizing container in accordance with claim 1, wherein the fluid channel with an end forming the channel inlet opening engages in a depression which is formed in the bottom and forms a fluid collection area for collecting fluid.

9. Sterilizing container in accordance with claim 1, wherein the channel outlet opening is directed at an upward flow side of the outlet valve.

10. Sterilizing container in accordance with claim 1, wherein:
    the fluid lifting device comprises an injector for lifting fluid through the fluid channel, and
    the injector comprises an injector inlet opening and an injector outlet opening, via which a flow connection is provided from a container interior defined by the sterilizing container to the outlet valve, and also an injector suction opening arranged in a direction of flow between the injector inlet opening and the injector outlet opening and formed by the fluid channel.

11. Sterilizing container in accordance with claim 10, wherein the injector is integrated in the fluid channel, the injector outlet opening being formed by the channel outlet opening and/or the injector inlet opening being formed in one of the first channel wall, the second channel wall, or a further channel wall of the fluid channel.

12. Sterilizing container in accordance with claim 1, wherein the fluid channel has a cross-sectional constriction.

13. Sterilizing container in accordance with claim 12, wherein in relation to a direction of flow of the fluid flowing from the bottom to the outlet valve, an inlet opening, via which a flow connection is provided from a container interior defined by the sterilizing container to the outlet valve, is formed upstream of the cross-sectional constriction in the fluid channel.

14. Sterilizing container in accordance with claim 1, wherein the fluid channel comprises a first channel section aligned in a direction facing away from the bottom, and, in relation to a direction of flow of the fluid flowing from the bottom to the outlet valve, downstream of the first channel section, a second channel section which includes an angle with the first channel section.

15. Sterilizing container in accordance with claim 14, wherein the first channel section is aligned at right angles or essentially at right angles to a set-down plane defined by the sterilizing container.

16. Sterilizing container in accordance with claim 14, wherein the second channel section has an inclination relative to a set-down plane defined by the sterilizing container.

17. Sterilizing container in accordance with claim 1, wherein the valve holder is detachably fixed to the container wall.

18. Sterilizing container in accordance with claim 1, wherein the valve device further comprises an inlet valve which is held on the valve holder.

19. Sterilizing container in accordance with claim 1, wherein:
    a further through-opening is formed in the container wall, and
    the valve device further comprises an inlet valve for opening and closing the further through-opening.

20. Fluid extraction device for use with a surgical sterilizing container having a container wall and a bottom, the fluid extraction device for extracting fluid from the sterilizing container comprising:
    a valve device comprising a pressure-actuatable outlet valve with which a through-opening formed in the container wall of the sterilizing container is openable and closable,
    a valve holder, which is fixed to the container wall, on which the outlet valve is held, and
    a fluid lifting device for providing a fluid connection from the bottom to the outlet valve, the fluid lifting device comprising a fluid channel for providing the fluid connection, through which fluid is liftable from the bottom to the outlet valve and comprising a channel inlet opening for the fluid and a channel outlet opening for the fluid,
    wherein:

the valve holder is fixed to the container wall from an inner side of the container,
the valve holder is inserted in the through-opening and forms a valve seat of the outlet valve,
the fluid channel is delimited by at least a first channel wall formed by the valve holder and a second channel wall which forms a cover covering the outlet valve on the inner side of the container, and
the through-opening is formed in the container wall and is at a distance from the bottom.

* * * * *